United States Patent
Shin et al.

(10) Patent No.: US 11,655,270 B2
(45) Date of Patent: May 23, 2023

(54) METHOD FOR SEPARATING COLLAGEN FROM LIPOSUCTION EFFLUENT USING SUPERCRITICAL PROCESS

(71) Applicant: DOF INC., Seongnam-si (KR)

(72) Inventors: YongWoo Shin, Seongnam-si (KR); Hyoung Soon Kim, Incheon (KR); Yoonkook Park, Sejong-si (KR); Yong-Soo Choi, Gunpo-si (KR); Kyu-byung Kim, Gwangju-si (KR); Seong Sik You, Pyeongtaek-si (KR); Gapsu Han, Seoul (KR); Seong-Rae No, Gwangju (KR)

(73) Assignee: DOF INC., Seongnam-Si (KR)

( * ) Notice: Subject to any disclaimer, the term of this patent is extended or adjusted under 35 U.S.C. 154(b) by 827 days.

(21) Appl. No.: 16/322,894

(22) PCT Filed: Aug. 8, 2017

(86) PCT No.: PCT/KR2017/008543
§ 371 (c)(1),
(2) Date: Feb. 1, 2019

(87) PCT Pub. No.: WO2018/030748
PCT Pub. Date: Feb. 15, 2018

(65) Prior Publication Data
US 2021/0332081 A1    Oct. 28, 2021

(30) Foreign Application Priority Data

Aug. 8, 2016 (KR) .......... 10-2016-0100641
Aug. 8, 2017 (KR) .......... 10-2017-0100339

(51) Int. Cl.
*C07K 1/14* (2006.01)
*B01D 11/02* (2006.01)
*C07K 14/78* (2006.01)

(52) U.S. Cl.
CPC ............ *C07K 1/14* (2013.01); *B01D 11/0203* (2013.01); *C07K 14/78* (2013.01)

(58) Field of Classification Search
CPC ......... A61K 35/35; F25J 1/0095; F25J 1/0042
See application file for complete search history.

(56) References Cited

U.S. PATENT DOCUMENTS

| | | | | |
|---|---|---|---|---|
| 5,261,612 A | * | 11/1993 | Ftaiha | A61L 27/24 241/46.06 |
| 8,007,718 B1 | * | 8/2011 | Biberger | B01J 25/02 422/28 |
| 10,881,761 B2 | * | 1/2021 | Wang | A61L 27/362 |
| 2003/0072677 A1 | * | 4/2003 | Kafesjian | A61L 27/3604 422/33 |
| 2003/0162707 A1 | | 8/2003 | Fraser et al. | |
| 2006/0292284 A1 | * | 12/2006 | Irwin | A23J 3/16 426/634 |
| 2013/0079494 A1 | | 3/2013 | Gleiman et al. | |
| 2014/0105856 A1 | * | 4/2014 | Schendel | A61K 35/28 424/85.2 |
| 2016/0159884 A1 | | 6/2016 | Schendel | |
| 2017/0144292 A1 | * | 5/2017 | Baskar | B25B 21/00 |

FOREIGN PATENT DOCUMENTS

| | | |
|---|---|---|
| KR | 10-0892605 B1 | 4/2009 |
| KR | 10-2011-0040977 A | 4/2011 |
| KR | 10-1105603 B1 | 1/2012 |
| KR | 10-2012-0111733 A | 10/2012 |
| KR | 10-2012-0120571 A | 11/2012 |
| KR | 10-2012-0134935 A | 12/2012 |
| KR | 10-1415367 B1 | 6/2014 |
| WO | WO-0077164 A1 * | 12/2000 .......... A61L 27/3604 |

OTHER PUBLICATIONS

Lamas D.L. (2015) Characterization of Proteolytic Enzymes from Sparus aurata L. Viscera, Obtained by Supercritical Carbon Dioxide, Mechanical and n-hexane Extraction Methods; J. Agric. Environ. Sci., vol. 4, No. 2, pp. 8-17.*
Cescon et al. (2015) Collagen VI at a glance, J. Cell Sci., vol. 128, pp. 3525-3531.*
Kim et al. (Human Collagen Isolated from Adipose Tissue, Biotechnol. Prog., 2012, vol. 28, No. 4, pp. 973-980).*
Glanville, Robert W. et al., Isolation and Characterization of a Native Placental Basement-Membrane Collagen and Its Component α Chains, Eur. J. Biochem. 95, 383-389 (1979).
Wang, et al., "Supercritical Carbon Dioxide Extracted Extracellular Matrix Material from Adipose Tissue," Materials Science and Engineering: C, 2017, pp. 349-358, vol. 75, 4 pages.
Lee, et al., "Development of Supercritical Fluid Processing and Technology," Report to the Department of Science and Technology, Korean government, 1996, 149 pages.
International Search Report of corresponding PCT/KR2017/008543, dated Nov. 8, 2017, 4 pages.

* cited by examiner

*Primary Examiner* — Suzanne M Noakes
*Assistant Examiner* — Jae W Lee
(74) *Attorney, Agent, or Firm* — Lewis Roca Rothgerber Christie LLP (57) ABSTRACT

The present invention relates to a method for extracting collagen from a liposuction effluent, wherein collagen is extracted by treating a collagen-containing liposuction effluent in the presence of a supercritical fluid. According to the present invention, conventionally discarded collagen in a liposuction effluent can be extracted at high purity, and the extracted high purity collagen can be widely used in medical, pharmaceutical, and cosmetic products.

1 Claim, 5 Drawing Sheets

METHOD FOR SEPARATING COLLAGEN FROM LIPOSUCTION EFFLUENT USING SUPERCRITICAL PROCESS

CROSS-REFERENCE TO RELATED APPLICATIONS

This application is a U.S. National Phase Patent Application and claims priority to and the benefit of International Application Number PCT/KR2017/008543, filed Aug. 8, 2017, which claims priority to and benefit of Korean Patent Application No. 10-2016-0100641 filed on Aug. 8, 2016, and Korean Patent Application No. 10-2017-0100339 filed on Aug. 8, 2017, the entire disclosures of which are incorporated by reference in their entirety.

TECHNICAL FIELD

The present invention relates to a method for extracting collagen, more specifically, a method for extracting collagen from a liposuction effluent, wherein collagen is extracted by treating a collagen-containing liposuction effluent in the presence of a supercritical fluid.

BACKGROUND ART

Collagen is a major protein in the connective tissue of the body, which takes up a very large portion of 25 to 35% of body composition proteins. Taking a look at the composition ratio of collagen in each part of the human body, collagen composes 18% of the dentin of teeth, 70% of the dermis under the skin epidermis, 50% of the articular cartilage, 80% of the organic matter of the bone, 80% of the tendons connecting the bones and muscles, and is a major constituent of the cornea and conjunctiva of eyes. The collagen found in animals is mostly Type I collagen, which is composed of a monomer of 300 kDa and has covalent bonds at specific sites.

Therefore, collagen found in mature tissues has low solubility. Further, the amino acids constituting the collagen are glutamic acid, hydroxyproline, glycine, proline, alanine and the like, wherein the content of hydroxyproline, which is specifically present only in collagen, is high.

Along with age, one loses the ability to synthesize collagen in the body. At about the age of 18, the rate of collagen production starts to drop rapidly, and at age 40, it is said to be less than half compared to that of age 18. In addition, as one gets older, metabolism slows down, and when old collagen does not decompose and accumulates continuously it causes lack of material needed for synthesizing collagen, thereby accelerating aging.

For this reason, in the field of food, cosmetics, and medicine, collagen development and development of cosmetics, edible materials and biological materials using collagen are being continuously studied. Collagen obtained from cattle and pigs has been mainly used until now, but after the outbreak of mad cow disease in cattle, collagen derived from fish and other livestock products other than cattle and pigs attracted attention and are being reviewed for use as a raw material for cosmetics, health foods, medicines and the like. Conventionally, methods for extracting common collagen from special parts of animals such as, types of fish such as squid, antler, chicken feet, and so on, in addition to livestock such as cattle and pigs, are known.

Korean Granted Patent Publication No. 10-892605 proposes a method for producing an extract having high collagen content for seasoning using chicken feet and a technique for utilizing the extract for seasoning. Here, a technique for producing an extract having high collagen content for seasoning is proposed, by bleaching and sterilizing chicken feet with a chlorine-based disinfectant, extracting proteins containing collagen by hydrothermal or proteolytic enzymes, and then filtering, separating, and concentrating the proteins.

Korean Patent Laid-Open Publication No. 2012-120571 discloses a method for producing collagen peptide, wherein a squid endothelium, which has undergone a pretreatment process in which squid endothelial parts are separated, selected and collected, washed with alkaline electrolytic water, and sterilized and disinfected with acidic electrolytic water, is dried to have a moisture content of 10 to 20% and pulverized, and then subject to hydrolysis using an enzyme to extract a collagen peptide and concentrated and spray-dried. In addition, in Korean Patent Laid-Open Publication No. 2012-134935, a method for extracting a collagen composition is proposed, wherein the method includes adding an aqueous solution of sodium hydroxide to squid skin powder made by drying and pulverizing, to remove non-collagen proteins, and after neutralizing and rinsing, adding water and nutraceutical enzyme to hydrolyze, and then secondary hydrolyzing using flavozymes enzyme and filtering and drying.

Korean Granted Patent Publication No. 10-1105603 proposes a method for treating collagen to have a high purity through acid dissolution in animal tissues, pepsin treatment, salt precipitation, filtration, secondary acid dissolution, secondary salt precipitation, phase separation and concentration, acid dissolution, and so on. Here, a method of recovering collagen removed using an enzyme, by softening an animal tissue with a hydrochloric acid solution and then using a pepsin enzyme and putting into a phosphoric acid to separate the collagen from the tissue and precipitating with sodium chloride, is proposed. Further, a method for producing a collagen solution, by dissolving the above-mentioned collagen again in a phosphoric acid solution, and after diluting the same, sterilizing filtering and then precipitating with salt to separate the collagen, and after removing moisture, pressurizing and concentrating the collagen precipitate and re-dissolving in a phosphoric acid solution and then neutralizing with a sodium hydroxide solution, is proposed.

In addition, as a method for obtaining human-derived collagen, a method of separating collagen through a 4-step process and then purifying with chromatography is reported (GLANVILLE, R W et al., Eur J Biochem, 95: 383, 1979), wherein in the 4-step process, the collagen contained in the placenta and the umbilical cord is subjected to a pepsin treatment, a fractionation method by salt precipitation, a carboxymethylation treatment, and then treated with pepsin again.

However, such a collagen extraction method is a typical extraction method using an acid and base treatment, an enzyme treatment, and so on, in which the process is complicated and the purity is poor. It is difficult to obtain high purity collagen from these conventional methods, and since the crude is derived from animals, it is inadequate for medical use on the human body.

Supercritical fluid extraction is a method of separating materials using a supercritical fluid having a gas-liquid nature that exists above a critical point, that is, above a critical temperature and a critical pressure. The supercritical fluid extraction is based on a combination of the principle of solvent extraction, in which soluble components contained in a crude are dissolved with a supercritical fluid due to a difference in solubility between the extraction crude and the supercritical fluid, and the principle of distillation, which is a phenomenon of evaporation in which the solute molecules contained in the crude shifts from a high density condensation phase to a supercritical fluid as a low density expansion phase. Such supercritical fluid extraction as described above enables the separation of various substances, such as isomers which are difficult to separate using conventional methods, separation of a heat denatured mixture, refining of a polymer material, separation of active ingredients from natural plants such as medicines and fragrances and so on. In addition, supercritical fluid extraction has the advantages of being harmless to the human body, and the solvent is inexpensive, and does not require an additional concentration process. Therefore, supercritical fluid extraction has been applied to various fields such as the medicine industry, food industry, cosmetics and perfume industry, chemical industry, energy industry and the like.

Generally, carbon dioxide is used as a supercritical fluid. This is because carbon dioxide has the advantages of having a low critical temperature (31° C.) and critical pressure (7.29 MPa), which allows easy adjustment to supercritical conditions, and is widely present in nature, colorless, odorless, harmless to the human body and chemically stable.

Meanwhile, adipose tissue occupies the most part in our body, and ⅓ to ⅔ of the adipose tissue is composed of adipose cells containing lipid and the rest is composed of adipocyte, vascular endothelial cells and preadipocyte. It is involved in the energy storage and metabolism of our body and exists around the skeleton, nerves, and cardiovascular system to play role of buffering external impact, and outside the protective membranes of important organs, plays a role to prevent adhesion therebetween. In addition, there is a very abundant microvascular network in the tissue, so it reacts sensitively to hormone and growth factors, and appearance wise, it is very important as an auxiliary role of the skeleton for maintaining the detailed contour and shape of shape of our body. In this way, the adipose tissue can be seen as one big organ rather than tissue in terms of the importance of its role. Further, since there are mesenchymal stem cells in adipose tissue as well as in bone marrow, recently, there have been active studies on inducing differentiation from adipose tissues to various mesodermal tissues.

Adipose tissue can be obtained by liposuction which is being performed for cosmetic purposes among obese patients recently. Liposuction has been performed with safe and easy procedures for the past 30 years. Generally, clinical liposuction can yield hundreds to thousands of ml of liposuction effluent at a time. In the past, these tissues have been discarded, but recently they have been used clinically for autologous fat transplantation and are being used by stem cell researchers to obtain stem cells.

These liposuction effluents contain not only stem cells but also large amounts of collagen which binds adipose tissue and connects the cells, but extraction methods for such collagen have not been established and so it is being discarded as is.

Accordingly, the present inventors have made intensive efforts to develop a method for extracting collagen derived from the human body with a high yield and high purity. As a result, it has been confirmed that a high purity collagen derived from the human body can be obtained when a supercritical extraction method using a human body-derived liposuction effluent is used, and so the present invention was completed.

SUMMARY OF THE INVENTION

The object of the present invention is to provide a method for extracting collagen from a liposuction effluent using a supercritical extraction method.

In order to achieve the above object, the present invention provides a method for extracting collagen from a liposuction effluent, characterized in that collagen is extracted by treating a liposuction effluent containing collagen in the presence of a supercritical fluid.

ABSTRACT

The present invention relates to a method for extracting collagen from a liposuction effluent, wherein collagen is extracted by treating a collagen-containing liposuction effluent in the presence of a supercritical fluid. According to the present invention, conventionally discarded collagen in a liposuction effluent can be extracted at high purity, and the extracted high purity collagen can be widely used in medical, pharmaceutical, and cosmetic products.

DETAILED DESCRIPTION OF THE INVENTION AND PREFERRED EMBODIMENTS

Unless otherwise defined, all technical and scientific terms used herein have the same meaning as commonly understood by one of ordinary skill in the art to which this invention belongs. In general, the nomenclature used herein is well known and commonly used in the art.

In the present invention, in order to extract high purity collagen from high quality collagen contained in a liposuction effluent that is discarded after a conventional plastic surgical liposuction, the collagen is extracted using carbon dioxide as a supercritical fluid.

Accordingly, an aspect of the present invention relates to a method for extracting collagen from a liposuction effluent characterized in that collagen is extracted by treating a liposuction effluent containing collagen in the presence of a supercritical fluid.

In the present invention, 'supercritical fluid' refers to a fluid that is in a gaseous state under normal conditions but is a fluid at or above a critical temperature or critical pressure.

The supercritical fluid suitable for use in the present invention is not particularly limited, but the supercritical fluid may be one selected from, the group consisting of a carbon dioxide gas, an ammonia gas, a nitrogen gas, a nitrogen monoxide (NO) gas, a nitrogen dioxide ($NO_2$) gas, a nitrous oxide ($N_2O$) gas, sulfur dioxide gas, hydrogen gas, water vapor, methane, ethylene, propane, propylene and a mixture thereof, alcohols including ethanol and methanol, and aromatic compounds including benzene and toluene. Preferably, carbon dioxide having a critical temperature of 31° C. and a critical pressure of 72.8 atm may be used.

The extraction method of the present invention may include, a method for extracting collagen from a liposuction effluent including, (a) filling a liposuction effluent containing collagen into a supercritical fluid extractor; (b) introducing a supercritical fluid into the extractor to extract a collagen-containing extract through a heat exchanger; and (c) decompressing a mixture of the supercritical fluid and the collagen-containing extract in a decompression separator for separating.

In the present invention, when carbon dioxide is used as a supercritical extract, it is preferable to use carbon dioxide in a condition wherein the temperature of the extraction step is preferably 10 to 50° C., and the pressure is preferably 100 to 500 bar.

In an embodiment of the present invention, a step of circulating the supercritical fluid separated in step (c) in a storage tank and then decompressing and recirculating together with an externally supplied supercritical fluid, and collecting a separated extract, may be further included.

In the present invention, 'auxiliary solvent' refers to a solvent other than the supercritical fluid that is added at the time of the supercritical fluid extraction.

In the present invention, an auxiliary solvent selected from the group consisting of ethanol, methanol, acetone, hexane, ethylacetate and methylene chloride may be further added as a co-solvent.

In the present invention, the supercritical fluid extraction temperature may be 10 to 50° C. and the pressure condition may be 100 to 500 bar.

In the present invention, the auxiliary solvent may be used in an amount of 1 to 500% (w/w) based on a crude to be extracted. Preferably, the auxiliary solvent is used in an amount of 50 to 200% (w/w) based on the crude to be extracted.

Further, the method of adding the auxiliary solvent to the extraction tank is not particularly limited. A method of a bottom-up extraction wherein the supercritical fluid and auxiliary solvent is added in a direction from the bottom of the extraction tank to the top so as to allow the extract to flow out to the top may be used, or oppositely, a method of a top-down extraction wherein the supercritical fluid and auxiliary solvent is added in a direction from the top to the bottom so as to allow the extract to flow out to the bottom of the extraction tank may be used as well.

The supercritical fluid extraction condition according to the present invention preferably has an extraction pressure of 72.8 to 500 atm and an extraction temperature of 31 to 100° C. More preferably, the extraction pressure is 100 to 400 atm and the extraction temperature is 35 to 65° C.

Another aspect of the present invention relates to a method for extracting collagen from a liposuction effluent using a supercritical fluid extraction including, (a) introducing a liposuction effluent into a supercritical extraction device and supplying $CO_2$, which is an extraction solvent, to an extraction reactor; (b) maintaining the pressure of the $CO_2$ supplied to the extraction reactor at 100 to 300 bar and the temperature at 10 to 50° C. to extract lipids through an outlet provided with a cooler; and (c) adjusting the pressure to normal pressure and separating the reactor to obtain collagen.

In the present invention, a solvent selected from the group consisting of ethanol, hexane, methanol, acetone, hexane, ethylacetate and methylene chloride may be further supplied as a co-solvent (auxiliary solvent).

In the present invention, the lipid is extracted in an oil phase, and the extracted lipid is lipid derived from lipid droplet of adipose tissue contained in the liposuction effluent, and includes triacylglycerol, sterol ester and the like.

Figure 1:
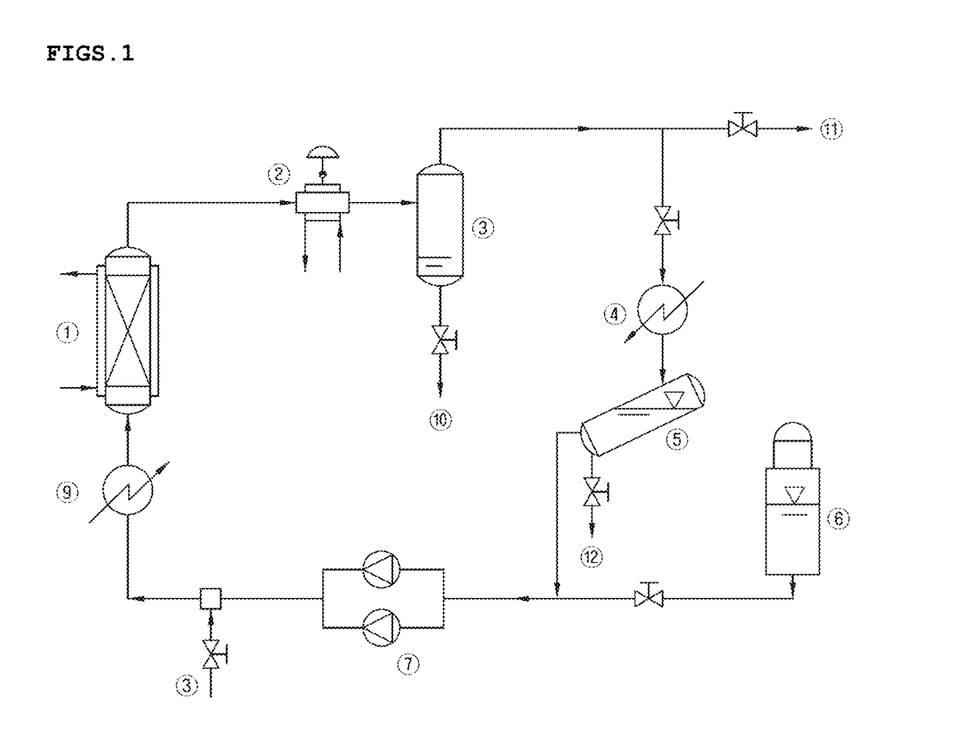
FIG. 1 shows a process of extracting collagen from a liposuction effluent using supercritical carbon dioxide.

Looking over a collagen extracting device according to the present invention in more detail, as shown in FIG. 1, an extractor ① is filled with a liposuction effluent and supercritical carbon dioxide suitably heated for extraction through a heat exchanger ⑨ is supplied to a lower end portion of the extractor ①. The supercritical carbon dioxide supplied in such a way comes into contact with the filled liposuction effluent to extract collagen and is discharged out of the extractor after rising. The extracted mixture of supercritical carbon dioxide and high purity collagen bypasses a decompression valve ② and is transferred to a decompressor ③ while being decompressed. At the decompressor ③, the extracted collagen and carbon dioxide is separated, and the separated carbon dioxide is liquefied as it passes a heat exchanger ④ and then is circulated to the storage tank ⑤ to be reused, and the collagen separated in the decompressor ③ is collected as a final product ⑩. In the carbon dioxide storage tank ⑥ other than the carbon dioxide that is circulated and supplied, to compensate for some loss that occurs in the previous process, carbon dioxide can be supplied from the outside. The carbon dioxide stored in the storage tank ⑤ is compressed through a pump ⑦ and is supplied to the extractor again through the heat exchanger ⑨ in a supercritical state. The auxiliary solvent is supplied though an auxiliary solvent inlet ⑧ as necessary.

This process can proceed continuously from the fat from liposuction until the desired collagen extraction yield is reached. Also, for continuous operation, two or more extractors ① are installed and they are used alternatively by controlling multiple supply valves and multiple discharge valves. In the extractor that is not being used, the crude that is done being extracted is removed and new liposuction effluent is filled to prepare for the next extraction.

In this regard, a method for extracting collagen using a supercritical fluid according to the present invention will be described.

A high-content, high-purity collagen extraction method using a supercritical fluid according to the present invention is configured as a process wherein, a liposuction effluent basically fills an extractor, a supercritical fluid is introduced in the extractor filled with the liposuction effluent to extract collagen, a mixture of the supercritical fluid and collagen that was extracted is separated by decompression, and the separated fluid is compressed and re-circulated by a pump.

At this time, in order to improve the extraction efficiency of the collagen, it is preferable to further add a pretreatment process of breaking the liposuction effluent into fine particles. In addition, although the supercritical fluid may be of various types, it is most preferable to use carbon dioxide. The pressure is preferably 100 to 500 bar, the temperature is preferably maintained at 10 to 50° C., and more preferably, the temperature is 20 to 50° C., and the pressure is maintained at 200 to 400 bar.

The collagen extracted by the present invention is advantageous in that it can be extracted in a polymer state as compared with collagen extracted by a conventional method.

Figure 4:
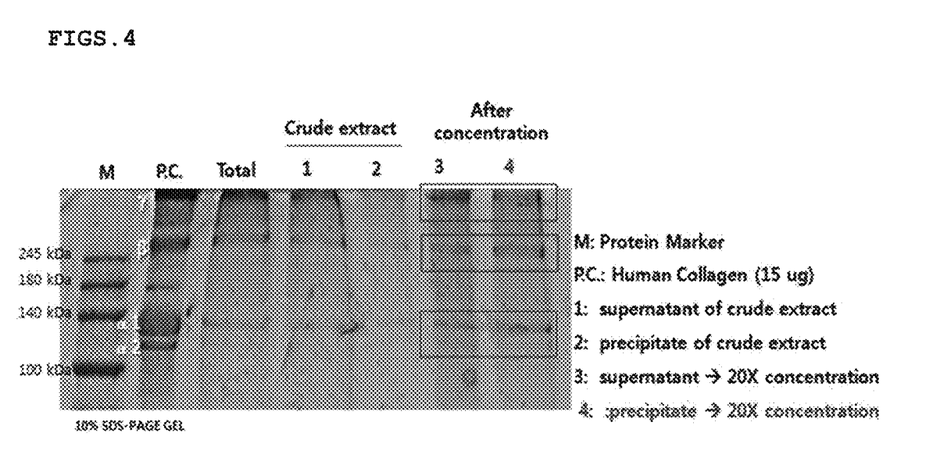
FIG. 4 shows the results confirmed through SDS-PAGE of collagen bands after concentrating separated collagen.
Figure 5:
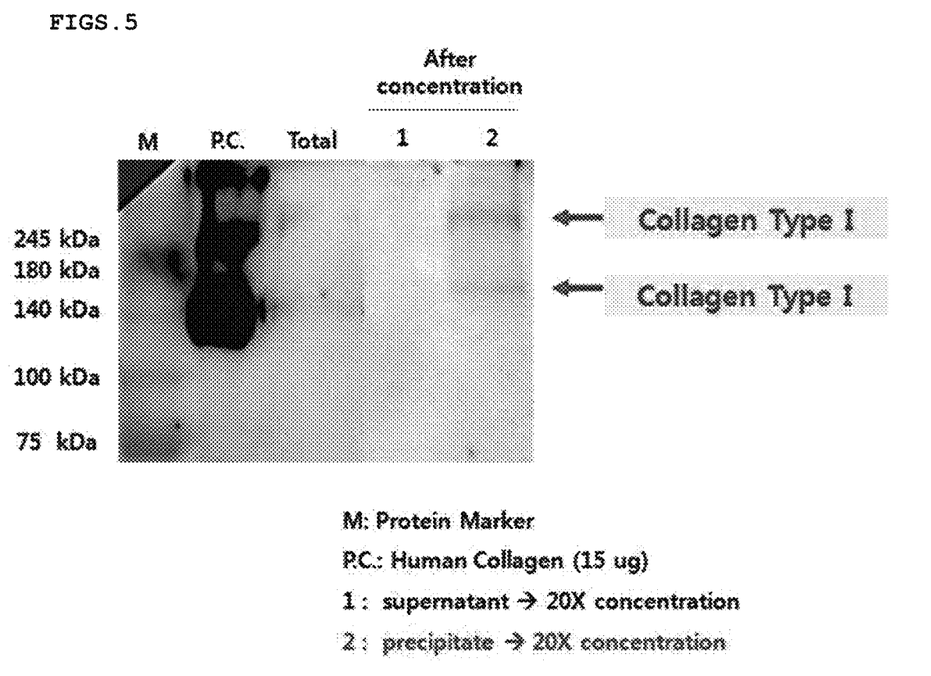
FIG. 5 shows the results confirmed through a Western blot analysis of a concentrated collagen sample.

In another embodiment of the present invention, a collagen band of a polymer was confirmed as the result of electrophoresis of a collagen separated by supercritical extraction (FIG. 2 and FIG. 4), and it was confirmed to be a Type 1 collagen through a Western blot analysis (FIG. 5).

In addition, the supercritical fluid extract prepared according to the method of the present invention can be manufactured into cosmetics such as lotion, essence and pack according to a known method. Lotions are generally based on purified water, ethanol and moisturizers. An acid, an alkali or an astringent agent is added thereto depending on the purpose. The essence refers to what contains a cosmetic ingredient having a skin moisturizing and anti-aging effects in a high concentration. The main constituents of essence are skin softener, moisturizer, solvent, emulsifier and thickener. The pack is used for the purpose of giving an appropriate tension to the skin and blocking the air from the outside to facilitate absorption of nutrients. The main components of the pack are film-forming agents, moisturizers, emulsifiers and solvents.

Finally, the supercritical fluid extract prepared according to the method of the present invention can be made into cosmetics having a gel or solid form according to a known method. The gel composition can be prepared by further mixing the above-mentioned solution composition with a thickener. The composition in solid form is comprised of emollients, thickeners, emulsifiers and solvents.

Hereinafter, the present invention will be described in more detail with reference to Examples. It should be apparent to those skilled in the art that these examples are merely illustrative of the present invention and that the scope of the present invention is not construed as being limited by these examples.

EXAMPLE

Example 1: Separation of Collagen from a Liposuction Effluent Using a Supercritical Fluid 100 ml of a liposuction sample was introduced into an extractor of a supercritical fluid extraction device configured as shown in FIG. 1 at a normal temperature and normal pressure. As a supercritical fluid, carbon dioxide was injected using a high pressure pump at 60 bar and −40° C., and a valve of the outlet was closed to gradually increase the pressure of a stirrer. A temperature sensor was provided inside the stirrer, and the internal temperature was maintained at a supercritical condition of 31° C. When the internal pressure became 250 bar, valve of the outlet was opened and at the same time, a booster was operated to inject high pressure carbon dioxide and the internal pressure was maintained at 250 bar.

In this case, the separated lipid in an oil state begins to be extracted at an outlet where the chiller is installed. If the oil spurt is low, the valve is adjusted at the outlet to raise the pressure to 300 bar and the pressure is maintained for 15 minutes. If additional oil is removed from the outlet, 30 minutes are waited for a complete removal of oil.

The pressure was gradually adjusted to normal pressure and the reactor was separated to extract the remaining tissues to confirm the presence or absence of collagen.

When co-solvent is used, 10 ml of 99.9% EtOH per 100 ml of fat is filled in the shear auxiliary tank of the agitator, and oil is extracted by the same process as above and collagen is separated.

Example 2: Confirmation of Supercritical Extracted Collagen by Electrophoresis

Figure 2:
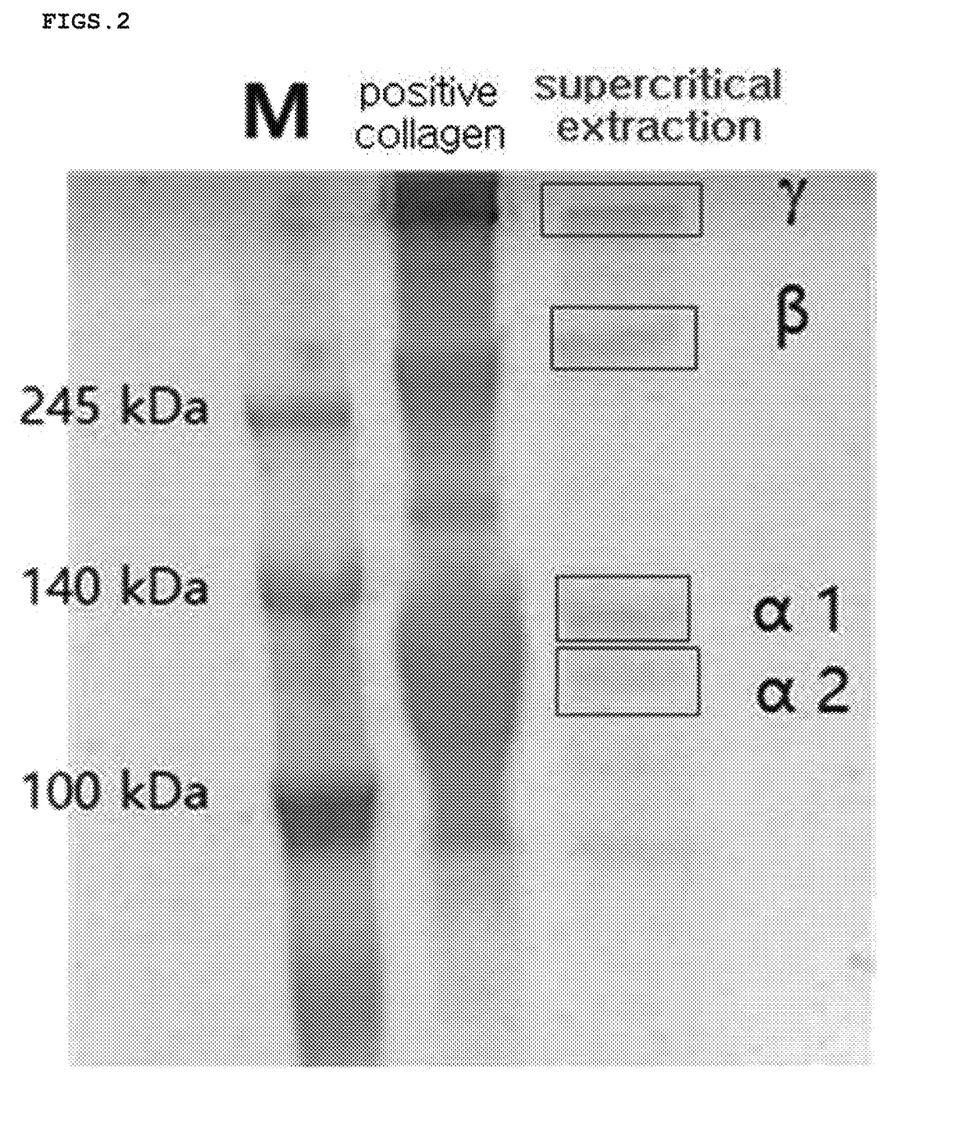
FIG. 2 shows the results confirmed through SDS-PAGE of collagen that was separated according to the present invention.

As a result of electrophoresis of the collagen separated by the supercritical extraction using SDS-PAGE, a collagen band was confirmed as shown in FIG. 2.

Figure 3:
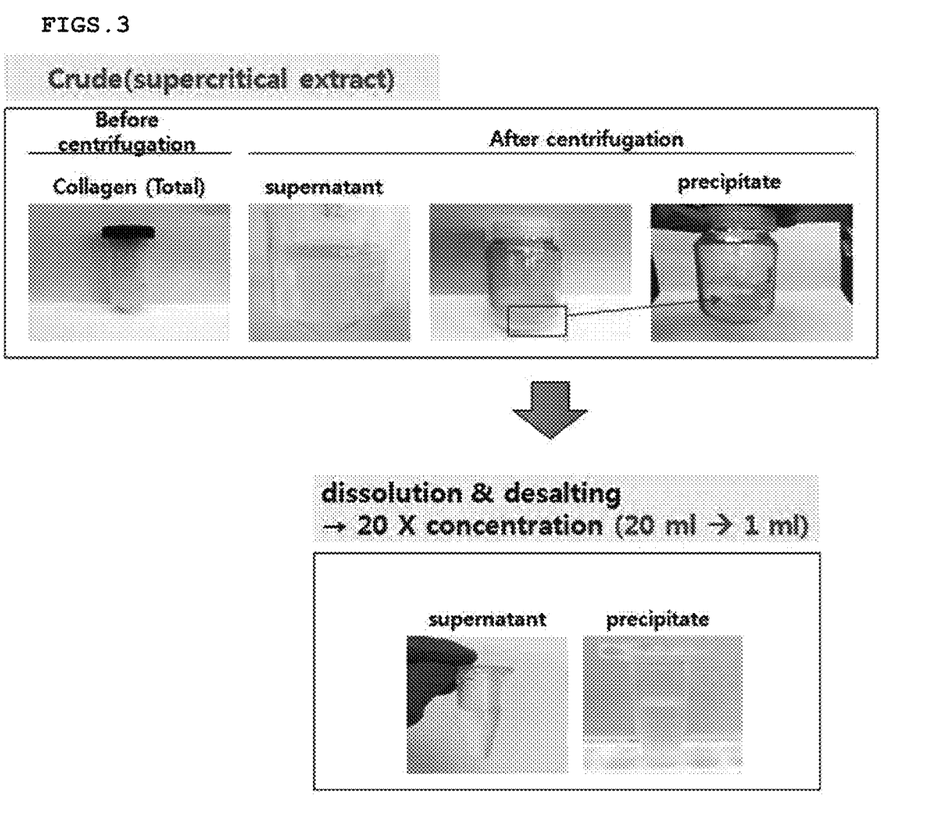
FIG. 3 shows a process of post-treating and concentrating collagen separated according to the present invention.

The supercritical extraction stock solution was separated by centrifugation, into a supernatant and a precipitate, and desalted and concentrated using an ultrafiltration device, and was concentrated to 20-fold (FIG. 3).

The concentration of protein in the total stock solution before concentration was measured by the Bradford method. With protein quantification using the Bradford method, collagen was not measured. The protein concentration of the whole stock solution was 0.239 (mg/ml), the protein concentration of the supernatant was 0.179 mg/ml, and protein was not detected in the precipitate (Table 1).

TABLE 1

| | Protein concentration (mg/ml) |
|---|---|
| Positive control group (positive collagen) | 0 |
| Whole stock solution | 0.239 |
| Supernatant | 0.179 |
| Precipitate | 0 |

SDS-PAGE was performed to confirm the presence or absence of collagen in the supernatant and precipitate after concentration. As a result, collagen was confirmed in the supernatant and precipitate before and after concentration, as shown in FIG. 4.

Example 3: Confirmation of Supercritical Extracted Collagen by Western Blot Analysis Western blot analysis was performed on the collagen extract supernatant and the precipitate concentrated in Example 2 to confirm the presence or absence of Type I collagen.

The supernatant and precipitate that was concentrated to 20-fold were electrophoresed on an 8% SDS-PAGE gel, and then a collagen band was moved to a nitrocellulose membrane, followed by Western blotting by treatment with a Type 1 collagen monoclonal antibody (Abcam, Cambridge, UK).

As a result, as shown in FIG. 5, a distinct Type 1 collagen protein band was confirmed in the 20-fold precipitate.

INDUSTRIAL APPLICABILITY

According to the present invention, collagen of a conventionally discarded liposuction effluent can be extracted in a polymer state having a high purity, and the extracted high purity collagen of the polymer can be widely used in medicine, pharmaceuticals, and cosmetics.

While the present invention has been particularly shown and described with reference to specific embodiments thereof, those skilled in the art will appreciate that such specific embodiments are merely preferred embodiments, it will be obvious that the scope of the present invention is not limited thereby. Accordingly, the actual scope of the present invention will be defined by the appended claims and their equivalents.

According to the present invention, collagen of a conventionally discarded liposuction effluent can be extracted in a polymer state having a high purity, and the extracted high purity collagen of the polymer can be widely used in medicine, pharmaceuticals, and cosmetics.

DESCRIPTION OF REFERENCE NUMERALS

① Extractor ② Decompression controller
③ $CO_2$—collagen separator ④ chiller
⑤ Liquefied $CO_2$ storage tank ⑥ CO2 supplement supply tank
⑦ $CO_2$ circulation pump ⑧ Auxiliary solvent inlet ⑨ Heat exchanger ⑩ High purity collagen-containing extract
⑪ CO2 vent ⑫ Removal of condensate

The invention claimed is:

1. A method for extracting Type I collagen in a polymer state from a liposuction effluent using supercritical fluid extraction comprising,
   (a) introducing a liposuction effluent into a supercritical extraction device and supplying $CO_2$, which is an extraction solvent, to an extraction reactor, and further adding ethanol as a co-solvent in an amount of 50 to 200% (w/w) with respect to the liposuction effluent;
   (b) maintaining the pressure of the $CO_2$ supplied to the extraction reactor at 200 to 300 bar and the temperature at 30 to 35° C. to extract lipids through an outlet provided with a cooler and remove the extracted lipids; and
   (c) adjusting the pressure to atmospheric pressure and separating the reactor to obtain the Type I collagen in the polymer state,
   wherein the molecular weight of the Type I collagen in the polymer state is 140 kDa or greater and 300 kDa or less.

* * * * *